US011246655B2

(12) United States Patent
de la Rama et al.

(10) Patent No.: US 11,246,655 B2
(45) Date of Patent: Feb. 15, 2022

(54) ABLATION CATHETER WITH ELECTRODES

(71) Applicant: St. Jude Medical, Cardiology Division, Inc., St. Paul, MN (US)

(72) Inventors: Alan de la Rama, Cerritos, CA (US); Peter Chen, Irvine, CA (US); Cary Hata, Irvine, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 294 days.

(21) Appl. No.: 15/542,030

(22) PCT Filed: Jan. 7, 2016

(86) PCT No.: PCT/US2016/012497
§ 371 (c)(1),
(2) Date: Jul. 6, 2017

(87) PCT Pub. No.: WO2016/112196
PCT Pub. Date: Jul. 14, 2016

(65) Prior Publication Data
US 2018/0000541 A1    Jan. 4, 2018

Related U.S. Application Data

(60) Provisional application No. 62/182,226, filed on Jun. 19, 2015, provisional application No. 62/100,843, filed on Jan. 7, 2015.

(51) Int. Cl.
*A61B 18/14*    (2006.01)
*A61B 5/287*    (2021.01)
(Continued)

(52) U.S. Cl.
CPC .......... *A61B 18/1492* (2013.01); *A61B 5/287* (2021.01); *A61B 2017/00053* (2013.01);
(Continued)

(58) Field of Classification Search
CPC ...... A61B 2017/00053; A61B 18/1492; A61B 2018/00351; A61B 5/0422;
(Continued)

(56) References Cited

U.S. PATENT DOCUMENTS 3,028,753 A     4/1962  Joy
6,522,932 B1 *  2/2003  Kuzma ................... A61N 1/05
                                                       607/116

(Continued)

FOREIGN PATENT DOCUMENTS

FR          2635066 A1     2/1990
WO       1998058681 A2    12/1998
(Continued)

OTHER PUBLICATIONS

ThomasNet, "Thermoset Polymers: Polyimide", 2011, p. 1, (Year: 2011).*

*Primary Examiner* — Eun Hwa Kim
*Assistant Examiner* — Adam Z Minchella
(74) *Attorney, Agent, or Firm* — Dykema Gossett PLLC (57) ABSTRACT

A catheter configured to deliver therapeutic energy to a tissue can include can include an elongate shaft extending along a shaft longitudinal axis and comprising a shaft proximal end and a shaft distal end. The catheter can include a flexible tip assembly comprising a tip assembly outer surface, wherein the flexible tip assembly is connected to the shaft distal end and is configured to deliver therapeutic energy to the tissue, and wherein the flexible tip assembly further includes. The flexible tip assembly can include an insulative layer comprising an insulative layer outer surface, wherein the insulative layer is disposed on the tip assembly outer surface and a mapping electrode disposed on the insulative layer outer surface.

6 Claims, 7 Drawing Sheets

(51) Int. Cl.
    *A61B 18/00* (2006.01)
    *A61B 17/00* (2006.01)
(52) U.S. Cl.
    CPC ............... *A61B 2018/00083* (2013.01); *A61B 2018/00351* (2013.01); *A61B 2018/00577* (2013.01); *A61B 2018/00839* (2013.01); *A61B 2562/02* (2013.01)
(58) Field of Classification Search
    CPC ........... A61B 2018/00083; A61B 2018/00577; A61B 2018/00839; A61B 2562/02
    See application file for complete search history.

(56) References Cited

U.S. PATENT DOCUMENTS

| | | | |
|---|---|---|---|
| 9,956,035 B2* | 5/2018 | Govari | A61B 18/1206 |
| 2004/0082860 A1* | 4/2004 | Haissaguerre | A61B 5/287 |
| | | | 600/466 |
| 2008/0294158 A1* | 11/2008 | Pappone | A61B 18/1492 |
| | | | 606/41 |
| 2009/0209950 A1* | 8/2009 | Starksen | A61B 5/0535 |
| | | | 606/21 |
| 2011/0313417 A1* | 12/2011 | De La Rama | A61B 18/1492 |
| | | | 606/41 |
| 2014/0058375 A1* | 2/2014 | Koblish | A61B 18/18 |
| | | | 606/33 |
| 2014/0081111 A1* | 3/2014 | Tun | A61B 5/6853 |
| | | | 600/374 |
| 2015/0374252 A1 | 12/2015 | de la Rama et al. | |

FOREIGN PATENT DOCUMENTS

| | | | | |
|---|---|---|---|---|
| WO | 2009089415 A1 | 7/2009 | | |
| WO | WO-2015185352 A1 * | 12/2015 | ........... | A61N 1/0492 |

* cited by examiner

ABLATION CATHETER WITH ELECTRODES

CROSS-REFERENCE TO RELATED APPLICATION

This application claims priority to U.S. provisional patent application No. 62/100,843, filed 7 Jan. 2015, and to U.S. provisional patent application No. 62/182,226, filed 19 Jun. 2015, both of which are hereby incorporated by reference as though fully set forth herein.

FIELD OF THE DISCLOSURE

This disclosure relates to an ablation catheter with electrodes.

BACKGROUND ART

Mapping and ablation catheters may be used for electrically mapping a body part and/or may be used to deliver therapy to a body part. In an example, the body part may include the heart and the delivery of therapy may include creating a lesion in heart tissue to treat conditions such as arrhythmia. A single point lesion, as its name implies, may be created by applying energy at a single point region of tissue. On the other hand, applying energy across an elongated region in a tissue creates a linear lesion.

BRIEF SUMMARY

In at least one embodiment, a catheter can include an elongate shaft extending along a shaft longitudinal axis and comprising a shaft proximal end and a shaft distal end. In at least one embodiment, a flexible tip assembly can comprise a tip assembly outer surface, wherein the flexible tip assembly is connected to the distal end of the elongate shaft and is configured to deliver therapeutic energy to the tissue. In at least one embodiment, an insulative layer can comprise an insulative layer outer surface, wherein the insulative layer is disposed on the tip assembly outer surface. In at least one embodiment, a mapping electrode can be disposed on the insulative layer outer surface.

In at least one embodiment, a catheter can include an elongate shaft comprising a shaft proximal end and a shaft distal end, the elongate shaft extending along a shaft longitudinal axis. In at least one embodiment, a tip assembly can comprise a tip assembly longitudinal axis and can be connected to the distal end of the elongate shaft. In at least one embodiment, the tip assembly can include a proximal electrode portion and a distal electrode portion connected to the proximal electrode portion via an intermediate portion, wherein the proximal, intermediate, and distal portions extend along the tip assembly longitudinal axis. In at least one embodiment, an insulative layer can be disposed on an outer surface of the intermediate portion. In at least one embodiment, a mapping electrode can be disposed on an outer surface of the insulative layer.

In at least one embodiment, a catheter tip assembly can include a proximal flexible electrode, wherein the proximal flexible electrode includes at least one first linear gap, configured to allow the proximal flexible electrode to flex. In at least one embodiment, an intermediate portion can be connected to a distal end of the proximal flexible electrode. In at least one embodiment, the intermediate portion can include an insulative layer circumferentially wrapped around an outer surface of the intermediate portion. In at least one embodiment, a plurality of mapping electrodes can be circumferentially disposed on an outer surface of the insulative layer. In at least one embodiment, the catheter tip assembly can include a distal flexible electrode connected to a distal end of the intermediate portion, wherein the distal flexible electrode includes at least one second linear gap, configured to allow the distal flexible electrode to flex.

DETAILED DESCRIPTION

The contents of U.S. Pat. No. 8,480,669 B2 entitled "Ablation Catheter with Flexible Tip;" U.S. Pat. No. 8,876,817 entitled "Electrophysiology System and Methods;" U.S. application Ser. No. 61/753,429 entitled "Flexible High-Density Mapping Catheter Tips and Flexible Ablation Catheter Tips with Onboard High-Density Mapping Electrodes;" U.S. application Ser. No. 13/836,846 entitled "Deflectable Catheter Shaft Section, Catheter Incorporating Same, and Method of Manufacturing Same;" U.S. Pat. No. 8,814,825 entitled "Deflectable Catheter Shaft Section, Catheter Incorporating Same, and Method of Manufacturing Same;" U.S. application Ser. No. 14/213,289 entitled "Flex Tip Fluid Lumen Assembly with Termination Tube;" U.S. application Ser. No. 14/333,235 entitled "Deflectable Catheter Shaft Section, Catheter Shaft Incorporating Same, and Method of Manufacturing Same;" United States publication no. 2011/0313417 A1 entitled "Ablation Catheter Having Flexible Tip with Multiple Flexible Electrode Segments;" United States publication no. 2013/0085479 A1 entitled "Catheter Having Flexible Tip with Multiple Flexible Segments;" U.S. Pat. No. 8,974,454 B2 entitled "Kit for Non-Invasive Electrophysiology Procedures and Method of Its Use;" U.S. publication no. 2010/0286684 A1 entitled "Flexible High-Density Mapping Catheter Tips and Flexible Ablation Catheter Tips with Onboard High-Density Mapping Electrodes;" U.S. publication no. 2012/0010490 A1 entitled "Medical Devices Having Flexible Electrodes Mounted Thereon;" and U.S. application Ser. No. 62/100,843 entitled "Ablation Catheter with Electrodes are hereby incorporated by reference."

Cardiac radiofrequency (RF) ablation has become the first line therapy for many types of arrhythmias. In RF ablation, a first step may be to diagnose the electrical activities of the heart (mapping) to identify the origins of the arrhythmia using a diagnostic catheter. In more advanced ablation procedures, a more detailed electroanatomical mapping may be required. In most cases, mapping utilizes a separate diagnostic catheter or multiple electrodes proximal to the ablation electrode. There may be a lack of effectiveness associated with performance of atrial fibrillation (AF) ablation when using prior techniques, due to the inability to analyze electrical activity at the precise targeted ablation sites and in real time during ablation therapy.

Embodiments of the present disclosure provide for a mapping and ablation catheter. The catheter may provide for mapping functionality that possesses a higher resolution over prior mapping and ablation catheters. In an example, prior mapping catheters have used ring electrodes for obtaining electrograms and electroanatomical mapping. The ring electrodes may oftentimes be spaced several or more millimeters apart from one another along a shaft of the mapping and ablation catheter. A shaft of the catheter, as well as the ring electrodes, may be contacted with tissue (e.g., cardiac tissue) and electrical signals produced by the tissue may be picked up by the ring electrodes and/or an ablating electrode for determining conditions such as AF. Electrical signals produced by tissue (e.g., cardiac tissue) that is located between the ring electrode and the ablating electrode may travel through a material separating the ring electrode and the ablating electrode. As the signals pass through the material, the signal may experience attenuation, which may involve a gradual loss in intensity of the signal as it passes through the material separating the ring electrode and the ablating electrode.

In addition, the ring electrodes of prior mapping and ablation catheters may be located along the shaft of the catheter and thus away from a direct site where ablation is occurring. As such, determining electrical signals produced by tissue that has been ablated may be made more complex, as the ring electrodes must be moved closer to the ablation site and/or an additional diagnostic catheter is placed at the ablation site to collect electrical signals produced by the tissue. In either case, determination of electrical signals at the precise ablation site may be difficult with prior mapping and ablation catheters.

Embodiments of the present disclosure provide for a mapping and ablation catheter. The catheter may provide for mapping functionality that possesses a higher resolution over prior mapping catheters, while simultaneously allowing for ablation functionality. In addition, the catheter may provide a determination of electrical signals at the ablation site.

Figure 1:
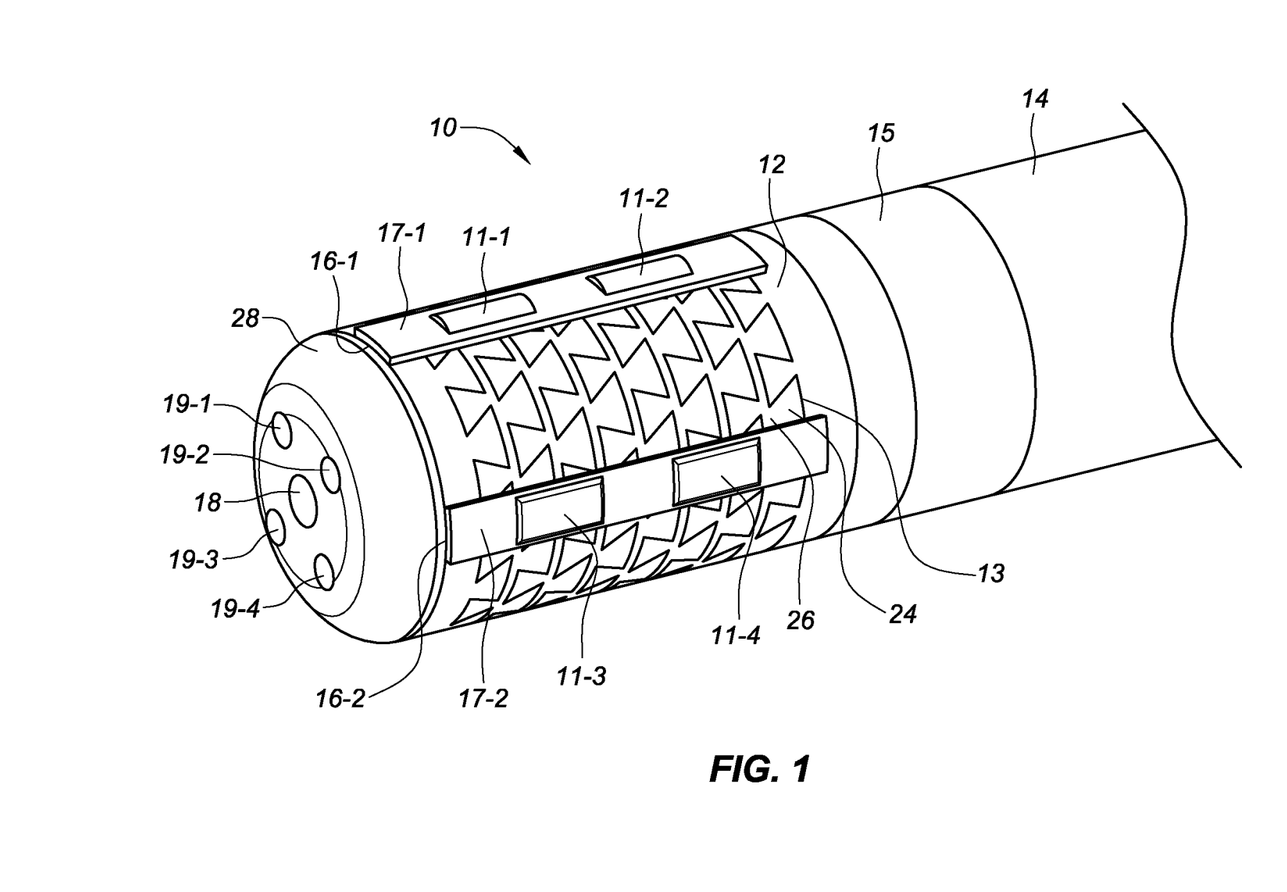
FIG. 1 is an isometric front, side, and top view of a flexible tip electrode with mapping electrodes, in accordance with embodiments of the present disclosure.

FIG. 1 is an isometric front, side, and top view of a flexible tip electrode 10, also referred to herein as flexible tip assembly, with mapping electrodes 11-1, 11-2, 11-3, 11-4, hereinafter collectively referred to as electrodes 11. The flexible tip electrode 10 may be attached to a distal end (e.g., shaft distal end) of a catheter shaft 14, in some embodiments, and may be formed from a metallic and/or conductive material. The catheter shaft 14 can be an elongate shaft that extends along a shaft longitudinal axis and comprises a shaft proximal end and a shaft distal end and may include a number of ring electrodes 15, as discussed herein, that may be used for mapping purposes in combination with the flexible tip electrode 10. The flexible tip electrode 10 may include an electrode wall 12 that may be formed of a radial surface and may include at least one linear gap 13. The at least one linear gap 13 may extend along an outer radial surface of the flexible tip electrode 10 and may form a variety of patterns on the outer radial surface of the flexible tip electrode 10, allowing for the flexible tip electrode 10 to flex and/or deform to some degree when a force is exerted on a tip of the flexible tip electrode 10, for example. In one embodiment, the pattern may be an interlocking dovetail pattern. The interlocking dovetail pattern may comprise a plurality of blocks wherein each of the blocks comprises a head 24 and a neck 26. Alternatively, in some embodiments, the pattern may be any type of interlocking arrangement that provides for relative movement in the proximal and distal direction with regard to either all or part of the catheter shaft 14. For example, alternative patterns of the interlocking arrangement may be bulbous, trapezoidal, triangular, rectangular, and/or another shape that creates an interlocking fit. In some embodiments, the at least one linear gap 13 can be configured to allow an irrigant to exit the flexible tip electrode from an inner lumen of the flexible tip electrode 10 via the at least one linear gap 13.

The flexible tip electrode 10 may include an electrode cap 20 that may be coupled to a distal end of the electrode wall 12. The electrode cap 20, in some embodiments, may include a plurality of irrigation ports 19 that pass through the electrode cap 20. The electrode cap 20 may include an electrode pocket 18, that may be configured to receive a distal end of a thermal sensor that passes through the flexible tip electrode 10.

In some embodiments, the flexible tip electrode 10 (e.g., flexible tip assembly) can comprise a tip electrode (e.g., tip assembly) outer surface (e.g., outer wall). In an example, the flexible tip electrode 10 may include channels 16-1, 16-2 that run along the flexible tip electrode 10 longitudinally, which are further discussed in relation to FIG. 2. The channels 16-1, 16-2 can be formed in the tip electrode 10 (e.g., tip assembly) outer surface. Hereinafter, channels 16-1, 16-2 are collectively referred to as channels 16. In an example, material may be removed from the outer wall 12 of the flexible tip electrode 10 to create the channels 16, each of which may have axially extending longitudinal walls that are parallel to one another and/or divergent to one another. In some embodiments, a base of the channel may be flat, convex, and/or concave. Material may be removed from the outer wall 12 of the flexible tip electrode 10 to create the channels 16 which may extend into the outer wall 12 toward a central axis of the flexible tip electrode 10.

Figure 2:
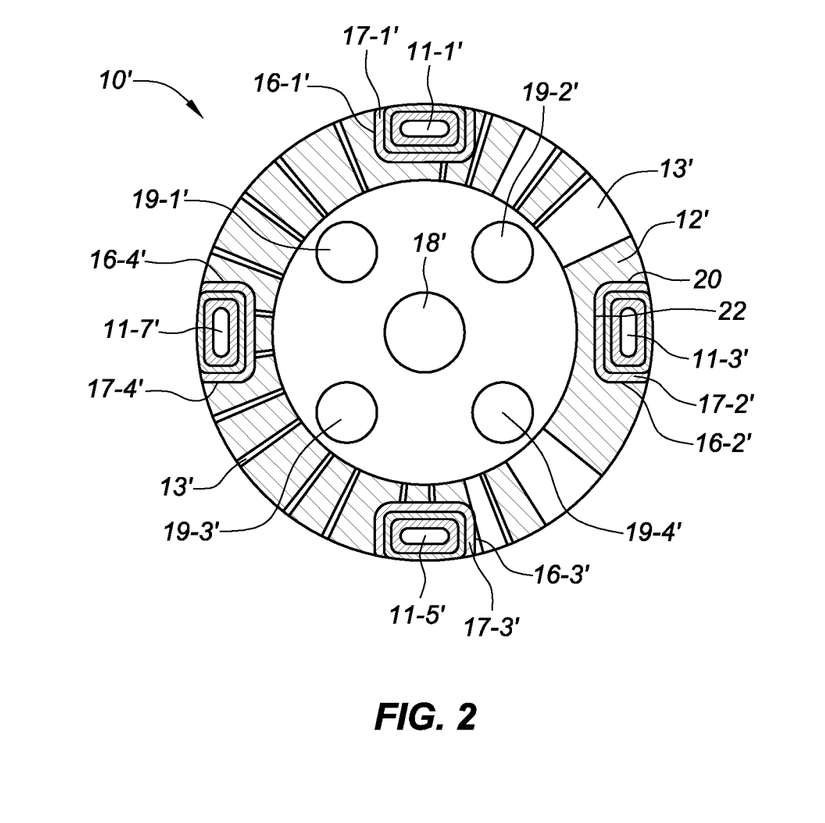
FIG. 2 is a cross-sectional front view of a flexible tip electrode with mapping electrodes, in accordance with embodiments of the present disclosure.

The channels 16-1, 16-2 may be formed in the outer wall 12 of the flexible tip electrode 10, such that the channels 16-1, 16-2 are located 90 degrees from one another (e.g., are formed in quadrants). In some embodiments, four channels may be formed in the outer wall 12 of the flexible tip electrode 10 and located 90 degrees from one another, such that pairs of channels are diametrically opposed from one another, which is discussed further in relation to FIG. 2. Although FIG. 1 depicts two channels 16, the flexible tip electrode 10 may include additional channels, as depicted in FIG. 2. For instance, an additional channel may be formed in the outer wall 12 of the flexible tip electrode 10 in a position that is diametrically opposed to a first channel 16-1. In some embodiments, an additional channel can be formed in the outer wall 12 of the flexible tip electrode 10 in a position that is diametrically opposed to a second channel 16-2.

In some embodiments, an insulative strip 17-1, 17-2 (e.g., insulative layer), hereinafter collectively referred to as insulative strips 17, may be disposed within the channels 16 and may run longitudinally along the flexible tip electrode 10. The insulative strip (e.g., insulative layer can comprise an insulative layer outer surface and can be disposed on the tip assembly (e.g., tip electrode 10) outer surface. The insulative strips 17 may be formed from a non-metallic material, which is insulative (e.g., does not readily conduct electricity) and is flexible. In some embodiments, the insulative strips 17 may cover the base of the channels 16, as well as the walls of the channels 16, and may include a cutout portion between the base of the channels 16 and the walls of the channels 16. In some embodiments, mapping electrodes 11 can be disposed on the insulative layer outer surface. In some examples, mapping electrodes 11 may be disposed within the cutout portion of the insulative strips 17, such that the mapping electrodes are longitudinally separated from one another. In an example, each insulative strip 17 may include individual cutouts for each mapping electrode 11. The mapping electrodes 11 may be wired through the tip, in some examples. For instance, wires may run through an inner cavity of the flexible tip electrode 10 and proximally along the catheter shaft 14. In some embodiments, the plurality of mapping electrodes 11 may be placed over a flexible non-metallic tube in order to provide isolation and to allow the mapping electrodes to simultaneously flex with the flexible tip electrode 10.

In some embodiments, the mapping electrodes 11 may be formed of various shapes, sizes, and materials. For example, the mapping electrodes 11 may be rectangular and/or cylindrical, among other shapes. In some embodiments, the mapping electrodes 11 may be elongated and extend longitudinally along the flexible tip electrode 10. In some embodiments, the electrodes 11 may be formed of a material that conducts electricity. For example, the electrodes 11 may be formed from a metallic material.

Although two mapping electrodes 11 are depicted in each channel 16, in FIG. 1, greater or fewer than two mapping electrodes 11 may be included in each channel. In addition, while four quadrants that each contain mapping electrodes 11 are discussed, fewer or greater than four quadrants that include mapping electrodes 11 may be included in the flexible tip electrode 10.

In some embodiments, the mapping electrodes 11 included in each channel 16 may be in longitudinal pairs. For example, as depicted in FIG. 1, channel 16-1 includes two mapping electrodes 11 that are spaced apart longitudinally from one another in the channel 16. In some embodiments, each channel 16 may include more than two mapping electrodes 11. For example, each channel 16 may include three, four, etc. mapping electrodes 11. The longitudinal pairs of mapping electrodes 11 may be disposed in different quadrants of the flexible tip electrode 10 and may be positioned radially with respect to a central longitudinal axis of the flexible tip electrode 10.

In some embodiments, the insulative strips 17 and/or the electrodes 11 may provide mechanical support to control a degree of compression and/or flexing of the flexible tip electrode 10. For instance, a size of the insulative strips 17 and/or the electrodes 11 may be selected to vary the degree of compression and/or flexing of the flexible tip electrode 10. Alternatively, a type of material that the insulative strips 17 and/or the electrodes 11 are made from may be selected to vary the degree of compression and/or flexing of the flexible tip electrode 10.

The mapping electrodes 11 included within the flexible tip electrode 10 may be used to pinpoint locations for ablation and to identify areas of interest for diagnosis and ablation and the flexible tip electrode 10 may improve contact with beating cardiac structures. This may allow the mapping electrodes 11 to remain in contact with tissue either endocardially or epicardially, improving the fidelity and resolution of the electrograms with minimal far-field signals.

Embodiments of the present disclosure may allow a physician to map the desired cardiac tissue in greater detail with higher resolution and ablate without losing the targeted sites. Unlike bipolar signals from the ablating tip and the adjacent ring electrode, the electrograms acquired from the mapping electrodes 11 may be directly from the tissue in contact with the flexible tip, which gives the user clearer electrogram attenuation in real time. The bipolar electrograms obtained from different combinations of mapping electrodes in configurations of the present disclosure may allow for directional assessment of the electrograms. In an example, electrogram recordings may be taken from the longitudinal pairs of mapping electrodes 11. For instance, an electrogram recording may be taken between the electrodes 11-1 and 11-2 and/or between the electrodes 11-3 and 11-4. Alternatively, electrogram readings may be taken between circumferential pairs of electrodes 11. For instance, an electrogram reading may be taken between electrodes 11-1 and 11-3, electrodes 11-3 and 11-5, electrodes 11-5 and 11-7, electrodes 11-7 and 11-1, electrodes 11-2 and 11-4, electrodes 11-1 and 11-4, electrodes 11-2 and 11-3, or any other combination of electrodes included on the flexible tip electrode 10. Additional electrodes 11-5, 11-6, 11-7, and 11-8 are hidden from view in FIG. 1.

In addition, embodiments of the present disclosure may provide for tissue assessment at the ablation site during or after an ablation procedure, since the mapping electrodes 11 are positioned proximate to the ablation site. This may provide valuable feedback to a physician in the form of an electrogram that is taken from an area where the ablation was performed, which may be analyzed to determine whether or not additional ablation of the area should be performed. For example, if gaps in the ablation have occurred, the mapping electrodes 11 may detect the gaps and additional ablation may be performed. In addition, embodiments of the present disclosure may determine a complete conduction block, conduction velocity vectors, as well as assess adjacent tissue.

FIG. 2 is a cross-sectional front view of a flexible tip electrode 10' with mapping electrodes 11-1', 11-3', 11-5', 11-7'. In an example, the cross-sectional front view depicted in FIG. 2 may be in a direction looking proximally towards the front of the flexible tip electrode 10'. The flexible tip electrode 10' may include one or more irrigation ports 19, as well as an electrode pocket 18, as discussed herein. The flexible tip electrode 10' can include at least one linear gap 13' formed in the outer wall 12'. In some embodiments, the flexible tip electrode 10' may include a number of channels 16' formed in the outer wall 12' of the flexible tip electrode 10', as discussed herein. In an example, four channels 16-1', 16-2', 16-3', 16-4', hereinafter collectively referred to as channels 16' may be formed in four quadrants of the outer wall of the flexible tip electrode 10'. In an example, each of the channels 16' may be positioned 90 degrees from one another, such that pairs of channels (e.g., 16-1' and 16-3', 16-2' and 16-4') are diametrically opposed from one another.

Insulative strips 17-1', 17-2', 17-3', 17-4', hereinafter collectively referred to as insulative strips 17', may be placed within the channels 16' and may include cutouts configured to accept mapping electrodes 11-1', 11-3', 11-5', 11-7', hereinafter collectively referred to as mapping electrodes 11'. In some embodiments, the channels 16' may be lined with an insulative material, that forms insulative strips 17'. For example, the insulative material can be disposed along sidewalls (e.g., sidewall 20) of the channels 16' (e.g., channel 16-2') and a bottom channel portion 22 of the channels 16' (e.g., channel 16-2'). Although not shown, one or more additional mapping electrodes 11' may be placed within the insulative strips 17' and channels 16', proximally with respect to the electrodes 11'. In an example, one additional mapping electrode may be placed behind (e.g., proximally with respect to) each of the mapping electrodes 11', such that each channel 16' includes a longitudinal pair of mapping electrodes 11' (e.g., longitudinal mapping electrode set). In some embodiments, the insulative strips 17' can be flush with an outer surface of the flexible tip electrode 10' and/or can extend from (e.g., radially from) an outer surface of the flexible tip electrode 10', as further depicted in FIG. 1.

The mapping electrodes 11' may be formed from one or more materials. For instance, as depicted in FIG. 2, the mapping electrodes 11' may be formed from multiple layers of different materials. In an example, and as depicted, the mapping electrodes 11' can include an inner core circumferentially surrounded by an intermediate layer and the intermediate layer can be circumferentially surrounded by an outer layer. Alternatively, the mapping electrodes 11' may be formed from one material. Each of the mapping electrodes 11' may be wired to a proximal end of the catheter shaft (e.g., a proximal electrical connector). In an example, the wires associated with each of the mapping electrodes 11' may travel through the catheter shaft. For instance, individual mapping electrodes 11' may be discretely wired and attached to an assigned pin of a connector located at a proximal end of a catheter handle.

Figure 3A:
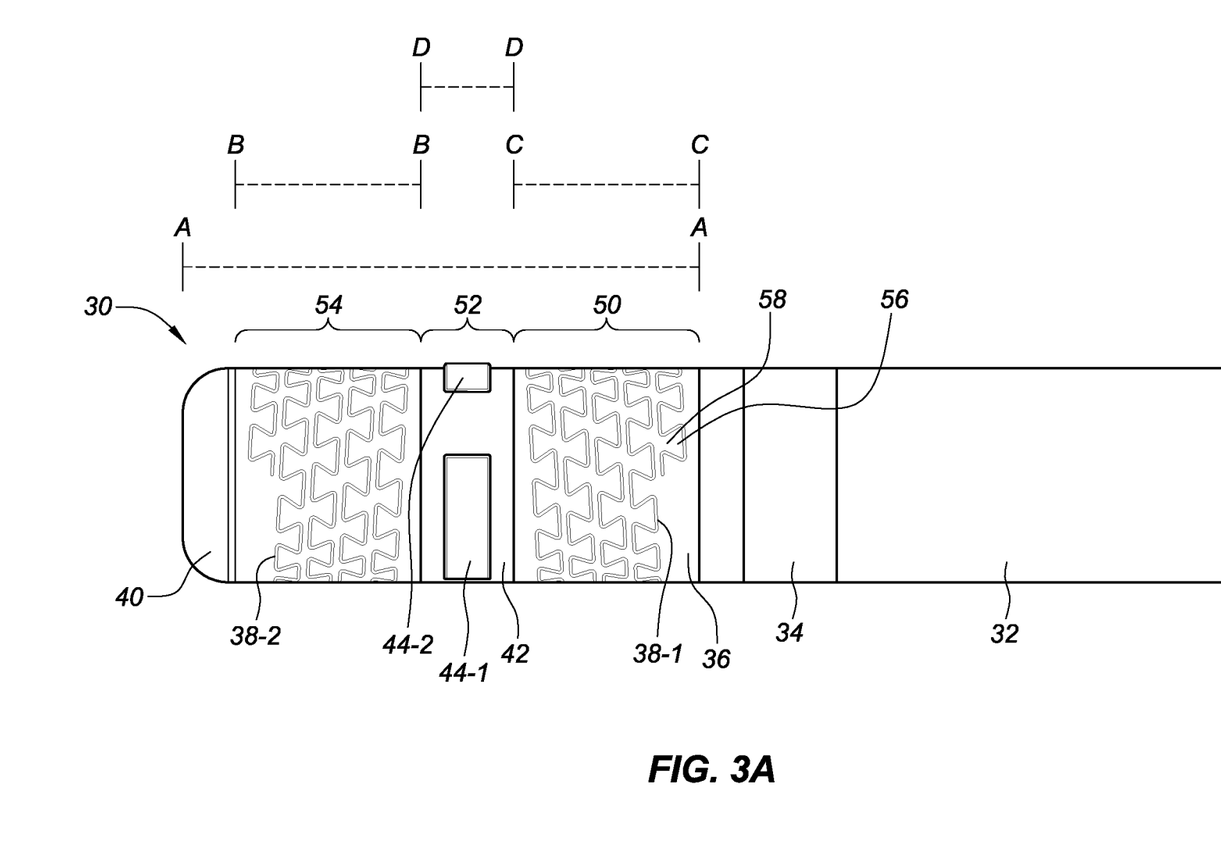
FIG. 3A is a side view of a second embodiment of a flexible tip electrode with mapping electrodes, in accordance with embodiments of the present disclosure.
Figure 3B:
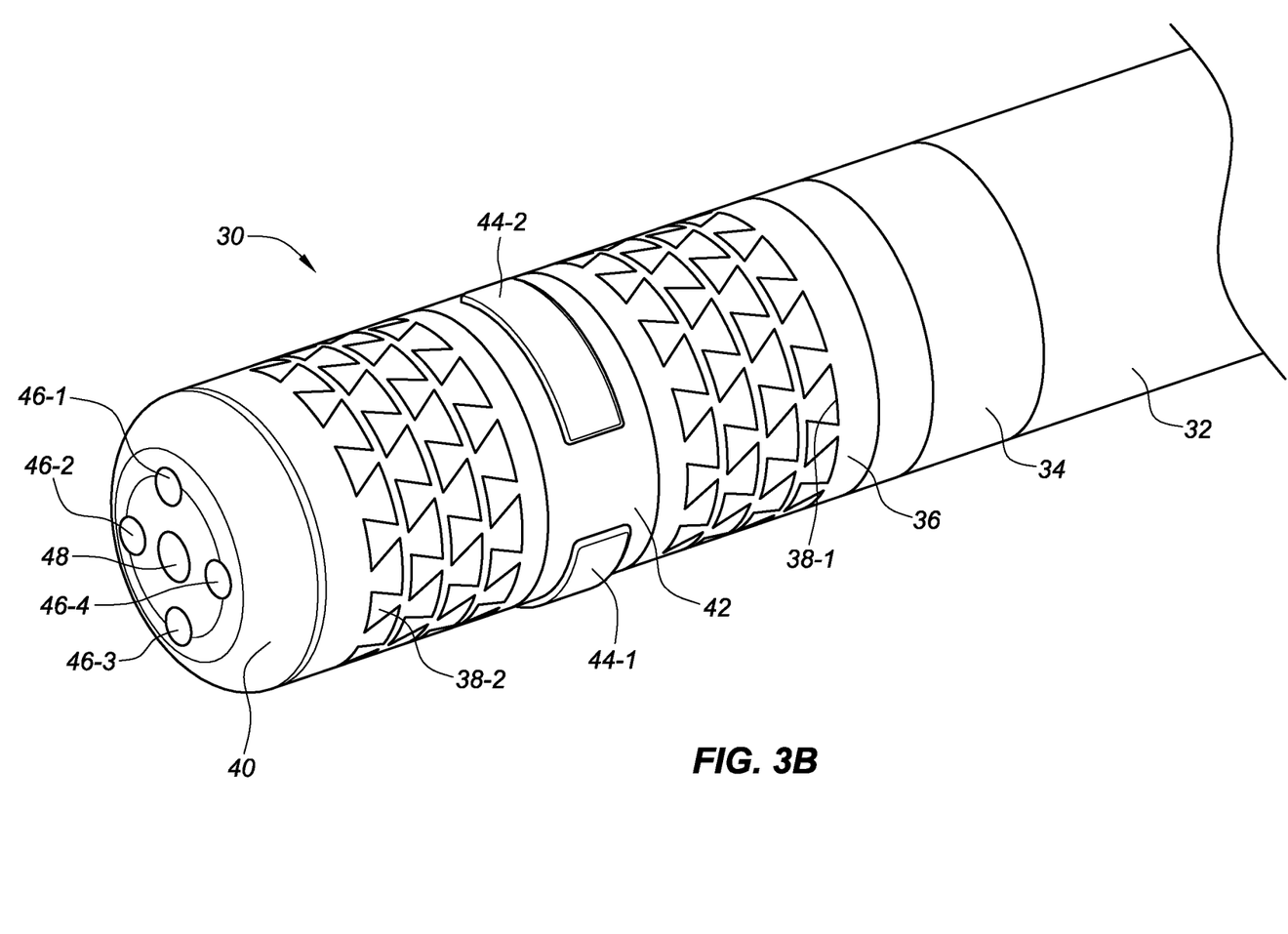
FIG. 3B is an isometric front, side, and top view of the second embodiment of the flexible tip electrode with mapping electrodes depicted in FIG. 3A, in accordance with embodiments of the present disclosure.
Figure 3C:
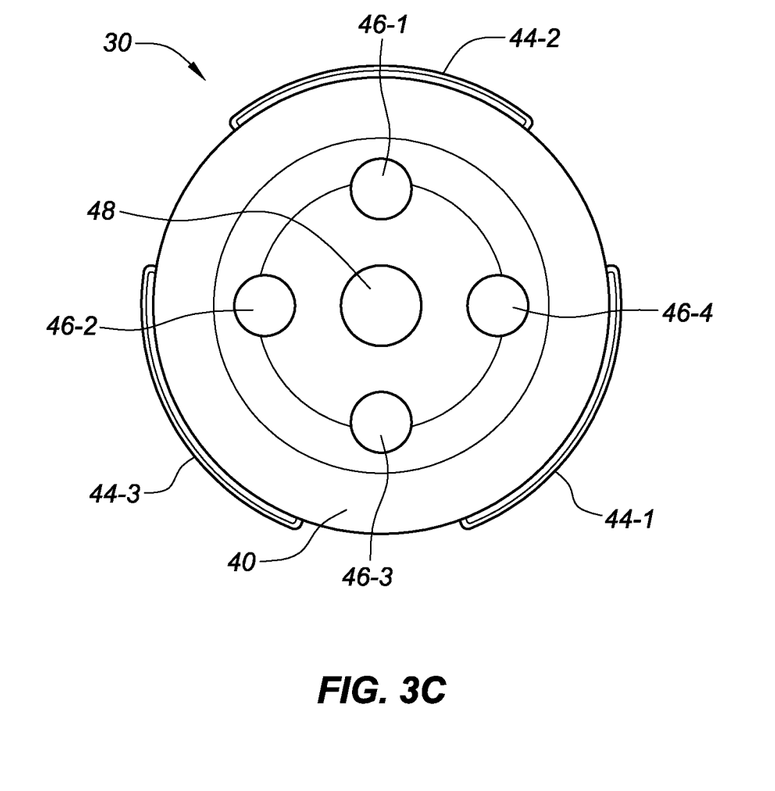
FIG. 3C is a front view of the second embodiment of the flexible tip electrode with mapping electrodes depicted in FIG. 3A, in accordance with embodiments of the present disclosure.

FIG. 3A is a side view of a second embodiment of a flexible tip electrode 30 with mapping electrodes 44-1, 44-2, in accordance with embodiments of the present disclosure (an additional mapping electrode 44-3 is depicted in FIG. 3C). The flexible tip electrode 30 may be attached to a distal end of a catheter shaft 32, and, in some embodiments, portions of the flexible tip electrode 30 may be formed from a metallic and/or conductive material. The catheter shaft 32 may include a number of ring electrodes 34, as discussed herein, that may be used for mapping purposes in combination with the flexible tip electrode 30. The flexible tip electrode 30 may include an electrode wall 36 that may be formed of a radial surface and may include at least one linear gap.

In some embodiments, the flexible tip electrode 30 can include a proximal portion 50, comprising at least one proximal linear gap 38-1 and a distal portion 54, comprising at least one distal linear gap 38-2. In an example, the proximal linear gap 38-1 can be formed in a proximal portion 50 of the electrode wall 36 defined by line C-C, as depicted, and the distal linear gap 38-2 can be formed in a distal portion 54 of the electrode wall 36 defined by line B-B, leaving an intermediate portion of the electrode wall 36 therebetween, defined by line D-D, that may not contain gaps. For example, the intermediate portion 52 (e.g., in a center of the proximal portion 50 and the distal portion 54) may not include linear gaps such as those included in the proximal portion 50 of the electrode wall 36 and the distal portion 54 of the electrode wall 36. The intermediate portion 52 of the electrode wall 36 located between the proximal linear gap 38-1 and the distal linear gap 38-2 may be a hollow cylindrical surface that is coaxial with a central longitudinal axis of the flexible tip electrode 30. Thus, the intermediate portion 52 of the electrode wall 36 can be rigid, which can allow for mounting of various devices, instruments, and/or sensors to the intermediate portion 52, as discussed herein. For example, the intermediate portion 52 of the electrode wall 36 can have a flexibility that is less than a flexibility associated with the proximal portion 50 of the electrode wall 36 (e.g., that includes the proximal linear gap 38-1) and/or a flexibility that is less than a flexibility associated with the distal portion 54 of the electrode wall 36 (e.g., that includes the distal linear gap 38-2).

The at least one proximal linear gap 38-1 and the at least one distal linear gap 38-2 may extend along an outer radial surface of the flexible tip electrode 30 and may form a variety of patterns on the outer radial surface of the flexible tip electrode 30, allowing for the flexible tip electrode 30 to flex and/or deform to some degree when a force is exerted on a tip of the flexible tip electrode 30, for example. As discussed herein, as the flexible tip electrode 30 flexes and/or deforms, the intermediate portion 52 of the flexible electrode tip defined by line DD can maintain its general shape allowing for various devices, instruments, and/or sensors to be connected to the intermediate portion 52 of the flexible tip electrode 30.

In some embodiments, the pattern associated with the at least one proximal linear gap 38-1 and the at least one distal linear gap 38-2 may be an interlocking dovetail pattern. The interlocking dovetail pattern may comprise a plurality of blocks wherein each of the blocks comprises a head 56 and a neck 58. Alternatively, in some embodiments, the pattern may be any type of interlocking arrangement that provides for relative movement in the proximal and distal direction with regard to either all or part of the catheter shaft 32. For example, alternative patterns of the interlocking arrangement may be bulbous, trapezoidal, triangular, rectangular, and/or another shape that creates an interlocking fit.

In some embodiments, the proximal linear gap 38-1 can have a different pattern than the distal linear gap 38-2. For example, the proximal linear gap 38-1 may have a dovetail, bulbous, trapezoidal, triangular, rectangular, and/or a pattern of another shape; and the distal linear gap 38-2 may have a dovetail, bulbous, trapezoidal, triangular, rectangular, and/or a pattern of another shape. In addition, the patterns between the proximal linear gap 38-1 and the distal linear gap 38-2 may be sized the same and/or differently from one another. For instance, the distal linear gap 38-2 can include a pattern (e.g., of a particular shape and/or size) that provides for an increased flexibility over the pattern (e.g., of a particular shape and/or size) associated with the proximal linear gap 38-1. Alternatively, the proximal linear gap 38-1 can include a pattern that provides for an increased flexibility over the pattern associated with the distal linear gap 38-2. The patterns between the proximal linear gap 38-1 and the distal linear gap 38-2 can be varied for other reasons, as well (e.g., to provide a difference in other characteristics, such as compression, etc.).

In some embodiments, the intermediate portion 52 of the flexible tip electrode 30 can be configured (e.g., tuned) to have a flexibility that is greater than a flexibility associated with the proximal linear gap 38-1 and/or distal linear gap 38-2. In an example, the distal linear gap 38-2 can have a flexibility that is greater than the intermediate portion 52 of the flexible tip electrode 30 and the intermediate portion 52 can have a flexibility that is greater than the proximal linear gap 38-1 of the flexible tip electrode 30. Alternatively, the proximal linear gap 38-1 can have a flexibility that is greater than the intermediate portion 52 and the intermediate portion 52 can have a flexibility that is greater than the distal linear gap 38-2. In some embodiments, the intermediate portion 52 can be configured to vary its flexibility by changing the axial length and/or the circumferential width of the mapping electrodes 44-1, 44-2, 44-3, and/or changing the length (e.g., axial length) of the intermediate portion 52. In some embodiments a shape of the mapping electrodes can be changed. For example, the mapping electrodes can be formed in a circular, triangular, oblong, or other type of pattern. In some embodiments, the material forming the insulative layer 42 can be changed to adjust the flexibility of the intermediate portion 52.

As discussed herein, the flexible tip electrode 30 may include an electrode cap 40 that may be coupled to a distal end of the electrode wall 36. The electrode cap 40, in some embodiments, may include a plurality of irrigation ports 46-1, 46-2, 46-3, 46-4 that pass through the electrode cap 40, as depicted in FIGS. 3B and 3C. The electrode cap 40 may include an electrode pocket 48, as depicted in FIGS. 3B and 3C, that may be configured to receive a distal end of a thermal sensor that passes through the flexible tip electrode 30. In some embodiments, an axial length of the flexible tip electrode 30, defined by line A-A can be approximately 5 millimeters, although the axial length of the flexible tip electrode 30 can be greater than or less than 5 millimeters.

In some embodiments, the proximal portion 50 of the electrode wall 36, defined by line C-C, can have an axial length of approximately 2 millimeters; the distal portion 54 of the electrode wall 36 defined by line B-B can have an axial length of approximately 2 millimeters; and the intermediate portion 52 of the electrode wall 36, defined by line D-D, can have an axial length of approximately 1 millimeter, although these dimensions are exemplary only and can be greater than or less than the lengths provided herein. However, in some embodiments, the proximal portion 50 can have a longer axial length than the distal portion 54. Alternatively, the distal portion 54 can have a longer axial length than the proximal portion 50. Thus, the intermediate portion 52 (and the mapping electrodes 44-1, 44-2, 44-3) can be moved proximally or distally along the flexible tip electrode 30. In some embodiments, an axial length of the mapping electrodes 44-1, 44-2, 44-3 can be approximately 0.5 millimeters, although the dimensions of the mapping electrodes can be greater than or less than 0.5 millimeters. The axial length of the mapping electrodes 44-1, 44-2, 44-3 be in a range of 0.5 to 2.0 millimeters. In some embodiments, the axial length of the mapping electrodes 44-1, 44-2, 44-3 can be in a range of 0.5 to 1.0 millimeters.

In some embodiments, one or more insulative strips 42 may be disposed around the intermediate portion 52 of the flexible tip electrode 30. The insulative strips 42 may be formed from a non-metallic material, which is insulative (e.g., does not readily conduct electricity) and is flexible, as discussed herein. In an example, the insulative strip 42 can extend axially between the proximal portion 50 of the flexible tip electrode 30 and the distal portion 54 of the flexible tip electrode 30 and can be circumferentially wrapped around the intermediate portion 52, such that it is concentric with the central longitudinal axis of the flexible tip electrode 30. In some embodiments, the insulative strip 42 can be a planar piece of material (e.g., in the shape of a rectangle), which can be wrapped around and connected to the intermediate portion 52 of the flexible tip electrode 30 to form a hollow cylinder that is concentric with the intermediate portion 52. Alternatively, the insulative strip 42 can be a hollow cylinder that is slid over and connected with the intermediate portion 52. In some embodiments, the intermediate portion 52 of the flexible tip electrode 30 where the insulative strip 42 is disposed can be recessed such that the outer radial surface of the electrode wall 36 is flush with an outer radial surface of the insulative strip 42.

In some embodiments, one or more mapping electrodes 44-1, 44-2, 44-3 can be disposed on the insulative strip 42 (e.g., around the outer radial surface of the intermediate portion 52 of the electrode wall 36). As depicted in FIGS. 3A-3C, three mapping electrodes 44-1, 44-2, 44-3 can be disposed on the insulative strip 42 (mapping electrode 44-3 is depicted in FIG. 3C). In some embodiments, the mapping electrodes 44-1, 44-2, 44-3 can be circumferentially disposed in tri-sectors around the flexible tip electrode 30, as depicted in FIGS. 3A to 3C. In some embodiments, the intermediate portion 52 of the flexible tip electrode 30 where the insulative strip 42 and mapping electrodes 44-1, 44-2, 44-3 are disposed can be recessed, such that the outer radial surface of the electrode wall 36 is flush with the outer radial surface of the insulative strip 42 and/or outer radial surface of the mapping electrodes 44-1, 44-2, 44-3.

As depicted, the mapping electrodes 44-1, 44-2, 44-3 can be planar strips (e.g., rectangles) that have a circumferential width that is greater than an axial length. The planar strips can be formed around the outer radial surface of the intermediate portion 52 of the electrode wall 36, such that a segmented ring electrode is formed (e.g., spaces exist between the mapping electrodes 44-1, 44-2, 44-3), in some embodiments. Although three mapping electrodes 44-1, 44-2, 44-3 are depicted, greater than or fewer than three mapping electrodes can be disposed around the outer radial surface of the intermediate portion 52 of the electrode wall 36. In some embodiments, the mapping electrodes 44-1, 44-2, 44-3 can be planar surfaces that have been formed as arcs, such that they wrap around the outer radial surface of the intermediate portion 52 of the electrode wall 36. However, the mapping electrodes 44-1, 44-2, 44-3 can be formed of various shapes, sizes, and materials. For example, the mapping electrodes 44-1, 44-2, 44-3 can be rectangular and/or cylindrical, among other shapes.

In some embodiments, the mapping electrodes 44-1, 44-2, 44-3 can be circumferentially spaced apart from one another such that the mapping electrodes 44-1, 44-2, 44-3 do not touch one another (e.g., a space exists between each of the mapping electrodes 44-1, 44-2, 44-3). In some embodiments, a ring electrode can be disposed around the intermediate portion 52 of the electrode wall 36. In an example, the ring electrode can circumferentially extend around the intermediate portion 52 of the electrode wall 36 such that it is coaxial with the central longitudinal axis of the flexible tip electrode 30. In some embodiments, the mapping electrodes 44-1, 44-2, 44-3 can be wired through the flexible tip electrode 30. For example, holes can be formed through a wall of the intermediate portion 52 of the electrode wall 36 and wires can extend from the mapping electrodes 44-1, 44-2, 44-3 through the wall of the intermediate portion 52, through the flexible tip electrode 30, and proximally through the catheter shaft 32.

FIG. 3B is an isometric front, side, and top view of the second embodiment of the flexible tip electrode 30 with mapping electrodes 44-1, 44-2, 44-3 depicted in FIG. 3A, in accordance with embodiments of the present disclosure. As depicted, the irrigation ports 46 can extend through the electrode cap 40. In addition, the electrode cap 40 can include an electrode pocket 48 that may be configured to receive the distal end of a thermal sensor (e.g., thermocouple) that passes through the flexible tip electrode 30.

FIG. 3B further depicts the mapping electrodes 44-1, 44-2 (mapping electrode 44-3 is hidden from view) circumferentially disposed in tri-sectors around the flexible tip electrode 30. As depicted, from the front, side, and top view of the flexible tip electrode 30, the mapping electrodes 44-1, 44-2 can be seen as conforming to a contour of the outer radial surface of the insulative strip and/or the outer radial surface of the intermediate portion 52 of the flexible tip electrode 30. For example, the mapping electrodes 44-1, 44-2, 44-3 can be arced, such that they are contoured to the outer radial surface of the insulative strip 42 and/or the outer radial surface of the intermediate portion 52 of the flexible tip electrode 30.

FIG. 3C is a front view of the second embodiment of the flexible tip electrode 30 with mapping electrodes 44-1, 44-2, 44-3, in accordance with embodiments of the present disclosure. As depicted, the mapping electrodes 44-1, 44-2, 44-3 are arced and thus conform to a contour of the outer radial surface of the insulative strip and/or outer radial surface of the intermediate portion 52 of the flexible tip electrode 30. In some embodiments, the mapping electrodes 44-1, 44-2, 44-3 can be high resolution electrodes. The mapping electrodes 44-1, 44-2, 44-3 can be circumferentially dispose in tri-sectors around the flexible tip electrode 30. In some embodiments, fewer than or greater than three mapping electrodes can be included on the flexible tip electrode 30, as discussed herein. The flexible tip electrode 30 can include an electrode cap 40, as depicted. The electrode cap 40 can include irrigation ports 46 and an electrode pocket 48, as discussed herein.

In some embodiments, as depicted in FIGS. 3A to 3C, the mapping electrodes 44-1, 44-2, 44-3 can be raised from an outer surface of the electrode wall 36. In some embodiments, the raised mapping electrodes 44-1 can help to ensure that when the flexible electrode tip 30 is in contact with tissue, the mapping electrodes 44-1, 44-2, 44-3 make sufficient contact with the tissue in order to perform diagnostic procedures (e.g., collect electrical signals from the tissue).

Figure 4A:
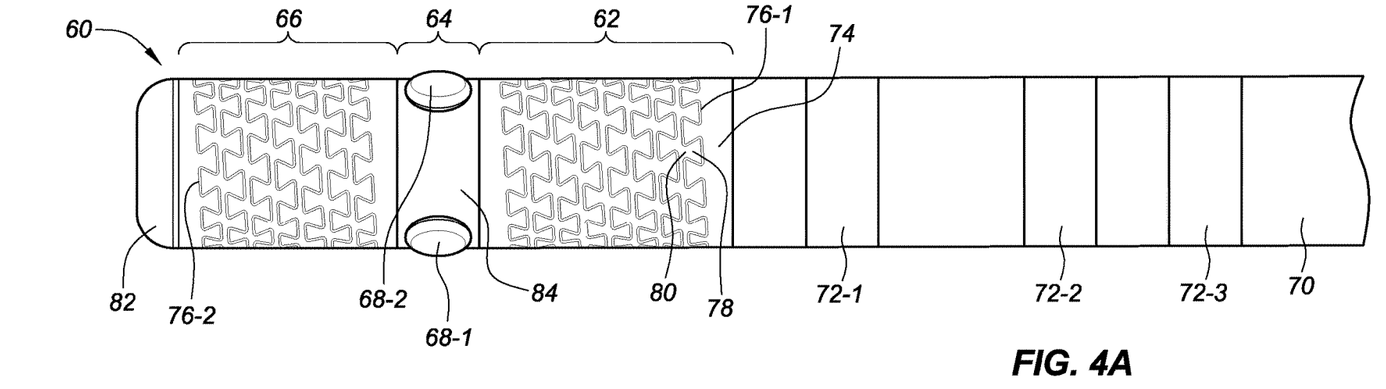
FIG. 4A is a side view of a third embodiment of a flexible tip electrode with mapping electrodes, in accordance with embodiments of the present disclosure.
Figure 4B:
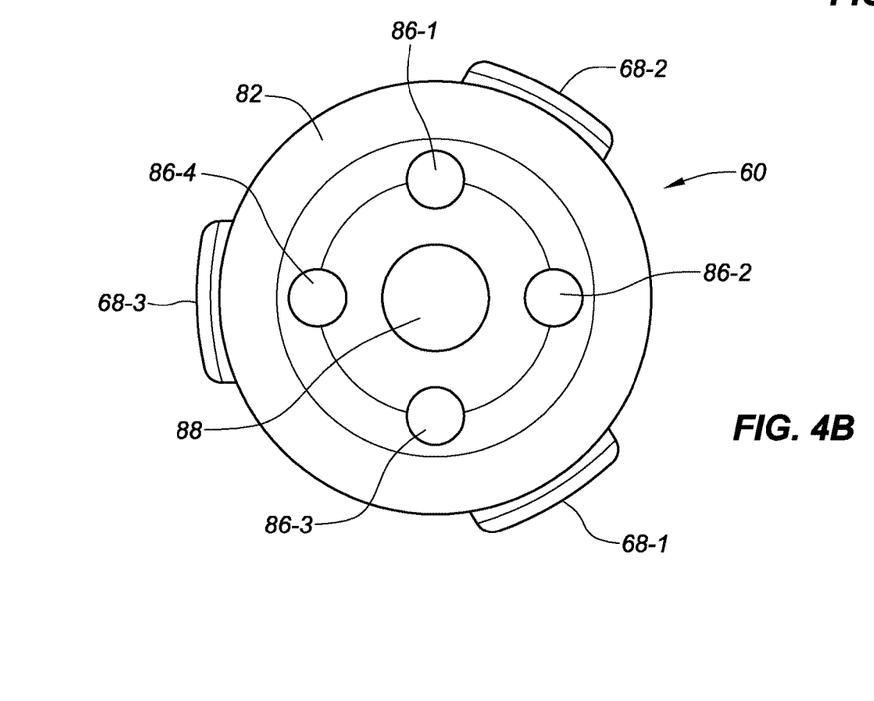
FIG. 4B is a frontal view of the third embodiment of the flexible tip electrode with mapping electrodes depicted in FIG. 4A, in accordance with embodiments of the present disclosure.

FIG. 4A is a side view of a third embodiment of a flexible tip electrode 60 with radiused mapping electrodes 68-1, 68-2, 68-3 (mapping electrode 68-3 is depicted in FIG. 4B), in accordance with embodiments of the present disclosure. The one or more embodiments included in FIG. 4 can include the same features as those previously discussed in relation to FIGS. 3A to 3C, with the addition of radiused mapping electrodes 68-1, 68-2, 68-3. The flexible tip electrode 60 may be attached to a distal end of a catheter shaft 70, in some embodiments; and portions of the flexible tip electrode 60 may be formed from a metallic and/or conductive material. The catheter shaft 70 may include a number of ring electrodes 72-1, 72-2, 72-3, as discussed herein, that may be used for mapping purposes in combination with the flexible tip electrode 60. The flexible tip electrode 60 may include an electrode wall 74 that may be formed of a radial surface and may include at least one linear gap.

In some embodiments, the flexible tip electrode 60 can include a proximal portion 62, comprising at least one proximal linear gap 76-1 and a distal portion 66, comprising at least one distal linear gap 76-2, as well as an electrode cap 82. An intermediate portion 64 can be disposed between the proximal portion 62 and the distal portion 66. The intermediate portion 64 may not include linear gaps, such as those included in the proximal portion 62 of the electrode wall 74 and the distal portion 66 of the electrode wall 74.

The intermediate portion 64 of the electrode wall 74 located between the proximal linear gap 76-1 and the distal linear gap 76-2 may be a hollow cylindrical surface that is coaxial with a central longitudinal axis of the flexible tip electrode 60. Thus, the intermediate portion 64 of the electrode wall 74 can be rigid, which can allow for mounting of various devices, instruments, and/or sensors to the intermediate portion 64, as discussed herein. For example, the intermediate portion 64 of the electrode wall 74 can have a flexibility that is less than a flexibility associated with the proximal portion 62 of the electrode wall 74 (e.g., that includes the proximal linear gap 76-1) and/or a flexibility that is less than a flexibility associated with the distal portion 66 of the electrode wall 74 (e.g., that includes the distal linear gap 76-2).

The at least one proximal linear gap 76-1 and the at least one distal linear gap 76-2 may extend along an outer radial surface of the flexible tip electrode 60 and may form a variety of patterns on the outer radial surface of the flexible tip electrode 60, allowing for the flexible tip electrode 60 to flex and/or deform to some degree when a force is exerted on a tip of the flexible tip electrode 60, for example. As discussed herein, as the flexible tip electrode 60 flexes and/or deforms, the intermediate portion 64 of the flexible tip electrode 60 can maintain its general shape allowing for various devices, instruments, and/or sensors to be connected to the intermediate portion 64 of the flexible tip electrode 60.

In some embodiments, the pattern associated with the at least one proximal linear gap 76-1 and the at least one distal linear gap 76-2 may be an interlocking dovetail pattern. The interlocking dovetail pattern may comprise a plurality of blocks wherein each of the blocks comprises a head 78 and a neck 80. Alternatively, in some embodiments, the pattern may be any type of interlocking arrangement that provides for relative movement in the proximal and distal direction with regard to either all or part of the catheter shaft 70. For example, alternative patterns of the interlocking arrangement may be bulbous, trapezoidal, triangular, rectangular, and/or another shape that creates an interlocking fit.

In some embodiments, the proximal linear gap 76-1 can have a different pattern than the distal linear gap 76-2, as discussed in relation to FIGS. 3A to 3C. In some embodiments, the intermediate portion 64 of the flexible tip electrode 60 can be configured (e.g., tuned) to have a flexibility that is greater than a flexibility associated with the proximal linear gap 76-1 and/or distal linear gap 76-2. In an example, the distal linear gap 76-2 can have a flexibility that is greater than the intermediate portion 64 of the flexible tip electrode 60 and the intermediate portion 64 can have a flexibility that is greater than the proximal linear gap 76-1 of the flexible tip electrode 60. Alternatively, the proximal linear gap 76-1 can have a flexibility that is greater than the intermediate portion 64 and the intermediate portion 64 can have a flexibility that is greater than the distal linear gap 76-2.

In some embodiments, one or more insulative strips 84 may be disposed around the intermediate portion 64 of the flexible tip electrode 60 and can include the same or similar properties with respect to the one or more insulative strips 42 discussed in relation to FIGS. 3A to 3C. In an example, the insulative strip 84 can extend axially between the proximal portion 62 of the flexible tip electrode 60 and the distal portion 66 of the flexible tip electrode 60 and can be circumferentially wrapped around the intermediate portion 64, such that it is concentric with the central longitudinal axis of the flexible tip electrode 60. In some embodiments, the insulative strip 84 can be a planar piece of material (e.g., in the shape of a rectangle), which can be wrapped around and connected to the intermediate portion 64 of the flexible tip electrode 60 to form a hollow cylinder that is concentric with the intermediate portion 64. Alternatively, the insulative strip 84 can be a hollow cylinder that is slid over and connected with the intermediate portion 64. In some embodiments, the intermediate portion 64 of the flexible tip electrode 60 where the insulative strip 84 is disposed can be recessed such that the outer radial surface of the electrode wall 74 is flush with an outer radial surface of the insulative strip 84.

In some embodiments, one or more radiused mapping electrodes 68-1, 68-2, 68-3 can be disposed on the insulative strip 84 (e.g., around the outer radial surface of the intermediate portion 64 of the electrode wall 74). As depicted in FIGS. 4A and 4B, three radiused mapping electrodes 68-1, 68-2, 68-3 can be disposed on the insulative strip 84 (mapping electrode 68-3 is depicted in FIG. 4B). FIG. 4B is a frontal view of the third embodiment of the flexible tip electrode with mapping electrodes depicted in FIG. 4A, in accordance with embodiments of the present disclosure.

In some embodiments, the mapping electrodes 68-1, 68-2, 68-3 can be circumferentially disposed in tri-sectors around the flexible tip electrode 60, as depicted in FIGS. 4A to 4B. Also depicted in FIG. 4B are irrigation ports 86-1, 86-2, 86-3, 86-4 that pass through the electrode cap 82 and an electrode pocket 88. In some embodiments, the intermediate portion 64 of the flexible tip electrode 60 where the insulative strip 84 and mapping electrodes 68-1, 68-2, 68-3 are disposed can be recessed, such that the outer radial surface of the electrode wall 74 is flush with the outer radial surface of the insulative strip 84.

As further depicted in FIGS. 4A and 4B, an outer face (e.g., exposed face) of the mapping electrodes 68-1, 68-2, 68-3 can be button shaped (e.g., dome shaped, having rounded circumferential edges, having radiused circumferential edges). In some embodiments, mapping electrodes can be cylindrical and can have 90 degree circumferential edges. The mapping electrodes 68-1, 68-2, 68-3 can be positioned around the outer radial surface of the intermediate portion 84 of the electrode wall 74, such that a segmented electrode is formed (e.g., spaces exist between the mapping electrodes 68-1, 68-2, 68-3), in some embodiments. Although three mapping electrodes 68-1, 68-2, 68-3 are depicted, greater than or fewer than three mapping electrodes can be disposed around the outer radial surface of the intermediate portion 84 of the electrode wall 74.

In some embodiments, the mapping electrodes 68-1, 68-2, 68-3 can be circumferentially spaced apart from one another such that the mapping electrodes 68-1, 68-2, 68-3 do not touch one another (e.g., a space exists between each of the mapping electrodes 68-1, 68-2, 68-3). For example, as depicted in FIG. 4B, the mapping electrodes 68-1, 68-2, 68-3 can be disposed in tri-sectors of the flexible tip electrode 60 (e.g., positioned approximately 120 degrees apart from one another). Although three mapping electrodes 68-1, 68-2, 68-3 are depicted, less than or greater than three mapping electrodes 68-1, 68-2, 68-3 can be disposed (e.g., circumferentially disposed) on the flexible tip electrode 60. In some embodiments, the mapping electrodes 68-1, 68-2, 68-3 can be wired through the flexible tip electrode 60. For example, holes can be formed through a wall of the intermediate portion 64 of the electrode wall 74 and wires can extend from each of the mapping electrodes 68-1, 68-2, 68-3 through the wall of the intermediate portion 64, through the flexible tip electrode 60, and proximally through the catheter shaft 70.

In some embodiments, one or more circumferential rows of mapping electrodes 68-1, 68-2, 68-3 can be disposed on the intermediate portion 84 of the flexible tip electrode 60. For example, while one circumferential row of mapping electrodes 68-1, 68-2, 68-3 is depicted in FIGS. 4A and 4B, one or more additional circumferential rows of mapping electrodes 68-1, 68-2, 68-3 can be positioned proximally or distally with respect to the circumferential row of electrodes 68-1, 68-2, 68-3. In some embodiments, an additional circumferential row of mapping electrodes can be radially offset from the circumferential row of mapping electrodes 68-1, 68-2, 68-3. For instance, with respect to FIG. 4B, each mapping electrode 68-1, 68-2, 68-3 is radially disposed from an adjacent mapping electrode by 120 degrees. In some embodiments, a second row of mapping electrodes can be disposed proximally and/or distally with respect to the set mapping electrodes 68-1, 68-2, 68-3 and radially disposed from the set by a particular amount (e.g., 60 degrees), which can provide a greater circumferential density of mapping electrodes.

Figure 5A:
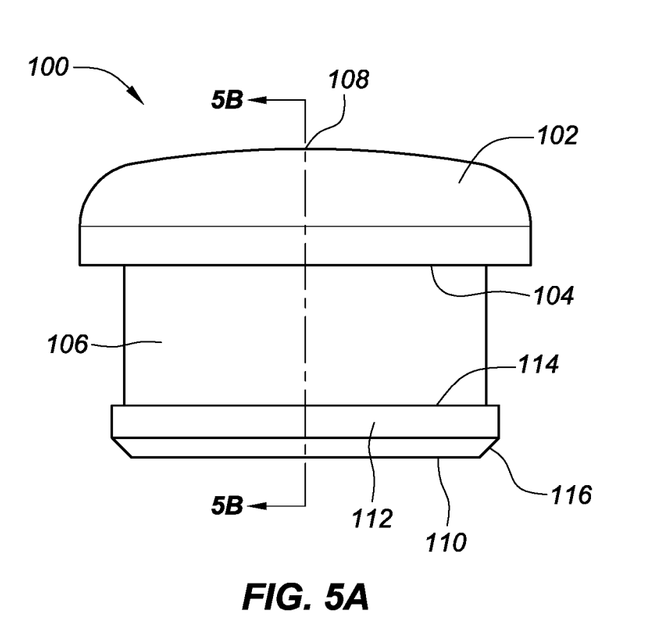
FIG. 5A is a radiused mapping electrode that includes a radiused electrode head, in accordance with embodiments of the present disclosure.

FIG. 5A depicts a radiused mapping electrode 100 that includes a radiused electrode head 102 (e.g., head portion), in accordance with embodiments of the present disclosure. The radiused mapping electrode 100 can include a distal end 108 and a proximal end 110. In an example, a distal end of radiused mapping electrodes 68-1, 68-2, 68-3 is depicted as protruding from (e.g., extending radially outward from) the insulative strip 84 in FIG. 4A. The radiused electrode head 102 can have a proximal circumferential lip 104 that extends around a proximal portion of the radiused electrode head 102. In some embodiments, distal circumferential edges of the radiused electrode head 102 can be radiused, as depicted in FIG. 5A.

In some embodiments, the radiused mapping electrode 100 can include a cylindrical intermediate portion 106 that extends proximally from the radiused electrode head 102 (e.g., radially inward from the radiused electrode head 102). The cylindrical intermediate portion 106 can have a diameter that is less than the radiused electrode head 102, in some embodiments. A proximal retainer base 112 can be disposed at a distal end of the cylindrical intermediate portion 106. The proximal retainer base 112 can include a distal circumferential lip 114 that is opposed to the proximal circumferential lip 104 of the radiused electrode head 102, which in some embodiments can include 90 degree circumferential edges for reasons further discussed herein. In some embodiments, the cylindrical intermediate portion 106 and the proximal retainer base 112 can form a body portion of the radiused mapping electrode 100.

Figure 5B:
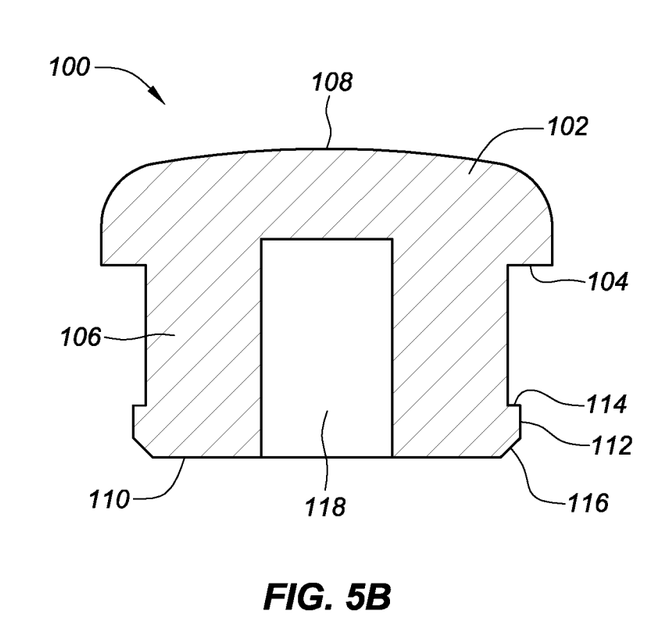
FIG. 5B is a cross-sectional view of the radiused mapping electrode taken along line 5B-5B, in FIG. 5A, in accordance with embodiments of the present disclosure.

The proximal retainer base 112 can include a radiused proximal circumferential lip 116, in some embodiments. In an example, the proximal circumferential lip 116 can be radiused at a 45 degree angle, although the proximal circumferential lip 116 can be radiused at other angles. In some embodiments, a diameter of the retainer base portion 112 can be greater than the diameter of the intermediate portion 106 and less than a diameter of the radiused electrode head 102. FIG. 5B depicts a cross-sectional view of the radiused mapping electrode 100 taken along line 5B-5B, in FIG. 5A, in accordance with embodiments of the present disclosure. As depicted, the radiused mapping electrode 100 can define a lumen extending distally into the radiused mapping electrode 100 along a longitudinal axis of the radiused mapping electrode 100 and from a proximal end of the radiused mapping electrode 100. In some embodiments, a lead (e.g., wire) can be inserted into the lumen and connected (e.g., soldered) to the radiused mapping electrode 100.

In some embodiments, the radiused mapping electrode 100 can be disposed in (e.g., inserted into) the insulative strip 84. For example, the insulative strip 84 can be disposed around the intermediate portion 106. In some embodiments, the retainer base portion 112 can have a diameter that is greater than the intermediate portion 106, but less than the radiused electrode head 102. In an example, the retainer base portion 112 and the radiused electrode head 102 can retain the radiused mapping electrode 100 in the insulative strip 84. In some embodiments, the insulative strip 84 can include a hole (e.g., circular hole) in which the radiused mapping electrode 100 can be disposed. In an example, a diameter of the hole can have a dimension that is less than the diameter of the retainer base portion 112. In some embodiments, the diameter of the hole in the insulative strip 84 can be sized and configured to engage an outer surface of the intermediate portion 106.

In some embodiments, the radiused mapping electrode 100 can be inserted into the hole formed in the insulative strip 84. For example, the proximal end 110 can be inserted into the hole formed in the insulative strip 84. In some embodiments, the insulative strip 84 can be formed of a deformable, flexible, semi-rigid, and/or rigid material. The radiused circumferential lip 116 can aid with insertion into the insulative strip 84. For example, the radiused circumferential lip 116 can reduce a resistance associated with inserting the radiused mapping electrode 100 into the insulative strip 84.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for an ablation catheter with electrodes has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A catheter configured to deliver therapeutic energy to a tissue, comprising:
    an elongate shaft extending along a shaft longitudinal axis and comprising a shaft proximal end and a shaft distal end;
    a flexible tip assembly comprising a tip assembly outer surface, wherein the flexible tip assembly is connected to the shaft distal end and is configured to deliver therapeutic energy to the tissue, and wherein the flexible tip assembly further includes:
        an electrode wall formed of a radial surface that includes at least one linear gap, wherein a plurality of separate insulated channels are defined in a surface of the electrode wall, wherein the linear gap is configured to allow the flexible tip assembly to flex and further configured to allow an irrigant to exit the flexible tip assembly from an inner lumen of the flexible tip assembly;
        a plurality of separate flexible insulative layers, each of the plurality of separate flexible insulative layers disposed in a respective one of the separate insulated channels defined in the surface of the electrode wall, wherein each separate insulated channel is defined by a longitudinally extending bottom channel surface and set of channel walls, wherein each of the plurality of separate flexible insulative layers line the bottom channel surface and the set of channel walls of the respective one of the separated insulated channels, thereby defining a plurality of separate insulated channels; and a plurality of mapping electrodes, each of the plurality of mapping electrodes disposed in a respective one of the separate insulated channels, wherein the plurality of separate insulated channels are configured to allow for flexing of a portion of the electrode wall on which the plurality of mapping electrodes are disposed.

2. The catheter of claim 1, wherein the flexible tip assembly comprises a tip assembly longitudinal axis, and wherein the plurality of insulative layers are elongated and extend along a longitudinal axis of the flexible tip assembly.

3. The catheter of claim 1, wherein a second plurality of mapping electrodes are disposed in the plurality of separate insulated channels to form a plurality of longitudinal mapping electrode sets.

4. The catheter of claim 3, wherein outer surfaces of the plurality of longitudinal mapping electrode sets are disposed evenly with the tip assembly outer surface and are circumferentially spaced apart.

5. The catheter of claim 4, wherein the plurality of longitudinal mapping electrode sets are equally spaced apart from one another.

6. The catheter of claim 1, further comprising a ring electrode disposed on the elongate shaft, proximally with respect to the flexible tip assembly.

* * * * *